United States Patent
Hensel et al.

(10) Patent No.: US 6,219,135 B1
(45) Date of Patent: Apr. 17, 2001

(54) DEVICE FOR OPTICALLY RECORDING, DIGITALLY, A PARAMETER ON A LONGITUDINALLY MOVED THREAD-TYPE MATERIAL

(75) Inventors: Rolf Hensel; Hans Wampfler, both of Zürich (CH); Jeffrey Mitchell Raynor, Edinburgh (GB); Peter Markus Seitz, Urdorf (CH)

(73) Assignee: Zellweger Luwa AG, Uster (CH)

( * ) Notice: Subject to any disclaimer, the term of this patent is extended or adjusted under 35 U.S.C. 154(b) by 0 days.

(21) Appl. No.: 09/242,477

(22) PCT Filed: Aug. 14, 1997

(86) PCT No.: PCT/CH97/00300

§ 371 Date: Jun. 29, 1999

§ 102(e) Date: Jun. 29, 1999

(87) PCT Pub. No.: WO98/08079

PCT Pub. Date: Feb. 26, 1998

(30) Foreign Application Priority Data

Aug. 20, 1996 (CH) .................................... 2030/96

(51) Int. Cl.[7] .................................................. G01N 21/00
(52) U.S. Cl. .................................. 356/238.2; 250/559.45; 250/559.48
(58) Field of Search ........................ 356/238.2, 429–431; 250/559.45–559.48

(56) References Cited

U.S. PATENT DOCUMENTS

| 4,812,043 | * | 3/1989 | Vanstaen .............................. 356/385 |
| 5,319,578 | * | 6/1994 | Lawson et al. ...................... 364/563 |
| 5,420,439 | * | 5/1995 | Landwehrkamp et al. .......... 250/572 |
| 5,499,794 | * | 3/1996 | Aeppli .............................. 250/559.45 |
| 5,615,014 | * | 3/1997 | Okuda .................................. 356/429 |
| 5,654,554 | * | 8/1997 | Feller et al. .................... 250/559.45 |

FOREIGN PATENT DOCUMENTS

| 643 060 | 5/1984 | (CH) . |
| 41 31 664 | 3/1993 | (DE) . |
| 0 553 445 | 8/1994 | (EP) . |

* cited by examiner

Primary Examiner—Frank G. Font
Assistant Examiner—Philip Natividad
(74) Attorney, Agent, or Firm—Burns, Doane, Swecker & Mathis L.L.P.

(57) ABSTRACT

The invention relates to a device and a method for the optical recording of at least one parameter on a longitudinally moved thread-type material. To enable parameters such as the diameter of a thread-type material, the diameter of a yarn package, the hairiness of a yarn etc. to be determined more simply and more accurately, an optical sensor composed of at least two individual sensors (30), in which at least one individual sensor is so constructed and arranged that at least one measured value is recorded digitally for a parameter, is to be used to record in parallel from the material at least two signals, one at least of which is clocked.

12 Claims, 5 Drawing Sheets

Figure 6:
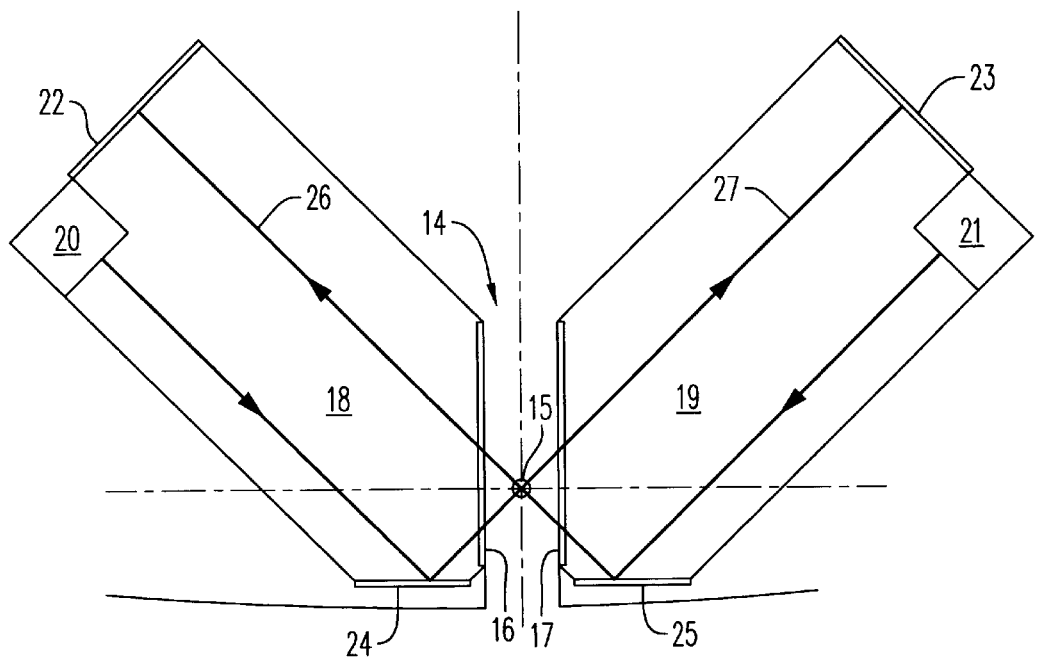

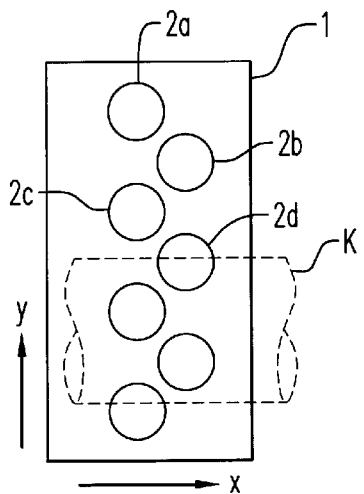
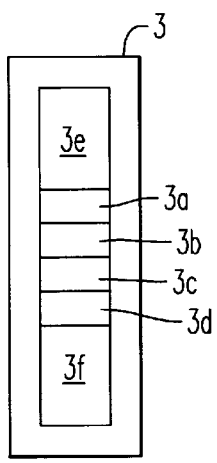
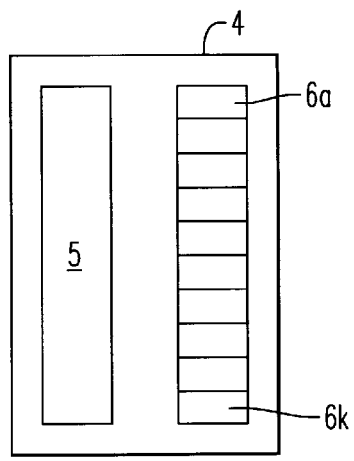
FIG. 1     FIG. 2     FIG. 3
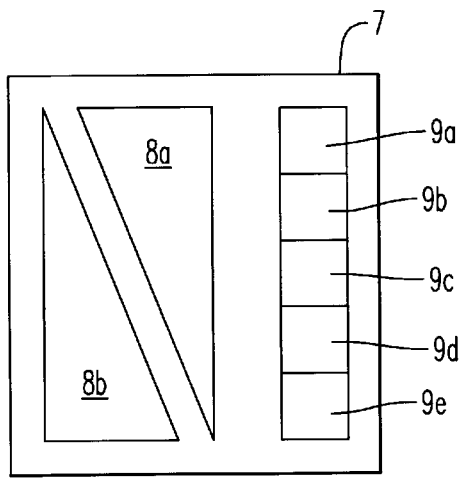
FIG. 4
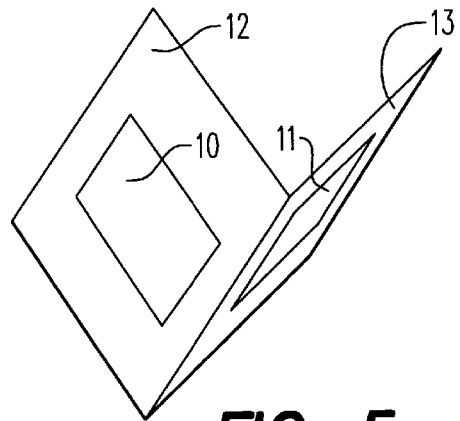
FIG. 5

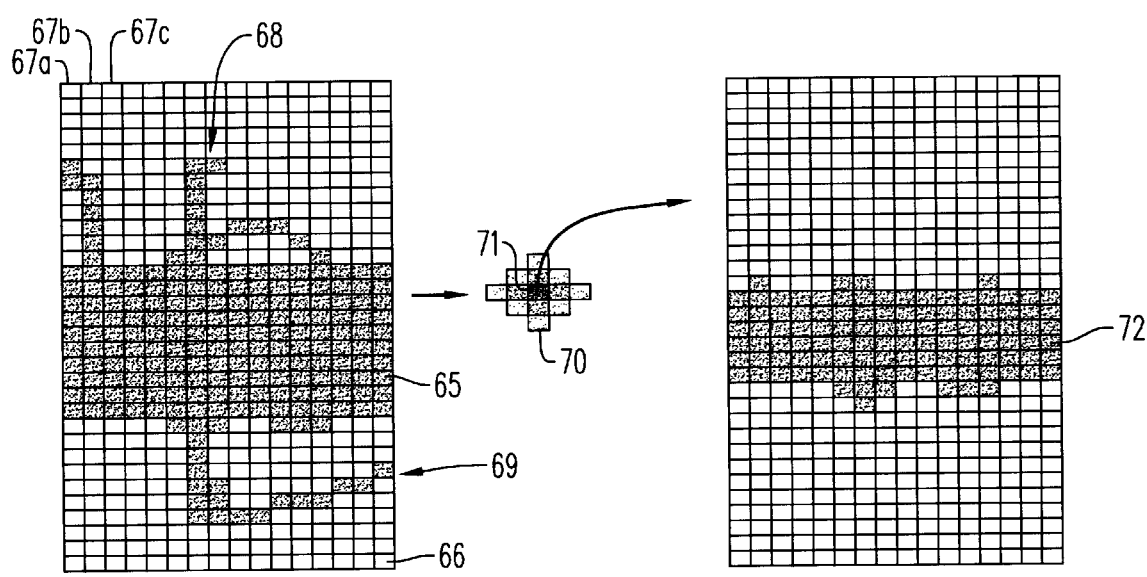
FIG. 12  FIG. 13

DEVICE FOR OPTICALLY RECORDING, DIGITALLY, A PARAMETER ON A LONGITUDINALLY MOVED THREAD-TYPE MATERIAL

The invention relates to a device for the optical recording of at least one parameter on a longitudinally moved thread-type material.

There is known from CH 643 060 a method and a device for determining the diameter or the cross-section of a thread or wire-type material. For this the shadows cast by the material irradiated by a light source are measured on an image recorder, which consists of a number of photocells arranged next to one another. The photocells emit pulse-type signals, which are evaluated together in an evaluation unit and converted into actual diameter and cross-section values.

It can be regarded as a disadvantage of this known method that for certain parameters precise measuring results have to be obtained with a correspondingly high amount of circuitry, since usable hairiness values for a yarn, for example, can be obtained with it only if the individual photocells have small dimensions and are provided in suitably large numbers.

The invention, as it is characterized in the claims, therefore solves the problem of creating a device with which parameters such as the diameter of a thread-type material, the diameter of a yarn package, the hairiness of a yarn etc., can be determined more simply and more precisely.

The problem is solved by an optical sensor composed of at least two individual sensors, in which at least one individual sensor is so constructed and arranged that at least one parameter is recorded digitally. Preferably the sensor thus comprises on the one hand individual sensors, which for example record directly digitally a parameter such as the diameter of the material and it comprises on the other an individual sensor which records the same or a different parameter by analog means. The sensor accordingly comprises individual sensors which operate according to different principles or whose signals are evaluated according to different principles. Said optical sensor has preferably an extent which exceeds hat of the material at right angles to its longitudinal direction and is preferably so constructed hat the recording of a parameter takes place at least partly in the same area of the material. the sensors are to be illuminated by directed light, so that the yarn shades off the light between the light source and the sensor. The sensor is connected to an evaluation circuit with which the signals from several individual sensors can also be evaluated jointly.

The advantages achieved by the invention can in particular be considered to reside in the fact that in addition to the diameter of a comparatively smooth material the diameter of a material with a broken surface structure can also be measured in a differentiated matter, without requiring a device that is of very elaborate construction. For example, there can be measured separately on a yarn the yarn package (without projecting fibers) and the hairiness (portion of projecting fibers) of the yarn. Such a sensor can also be adapted to changed measurement conditions by means of evaluation electronics and for example the effect on the sensors of dirt and deposits can be offset or allowed for.

Figure 10:
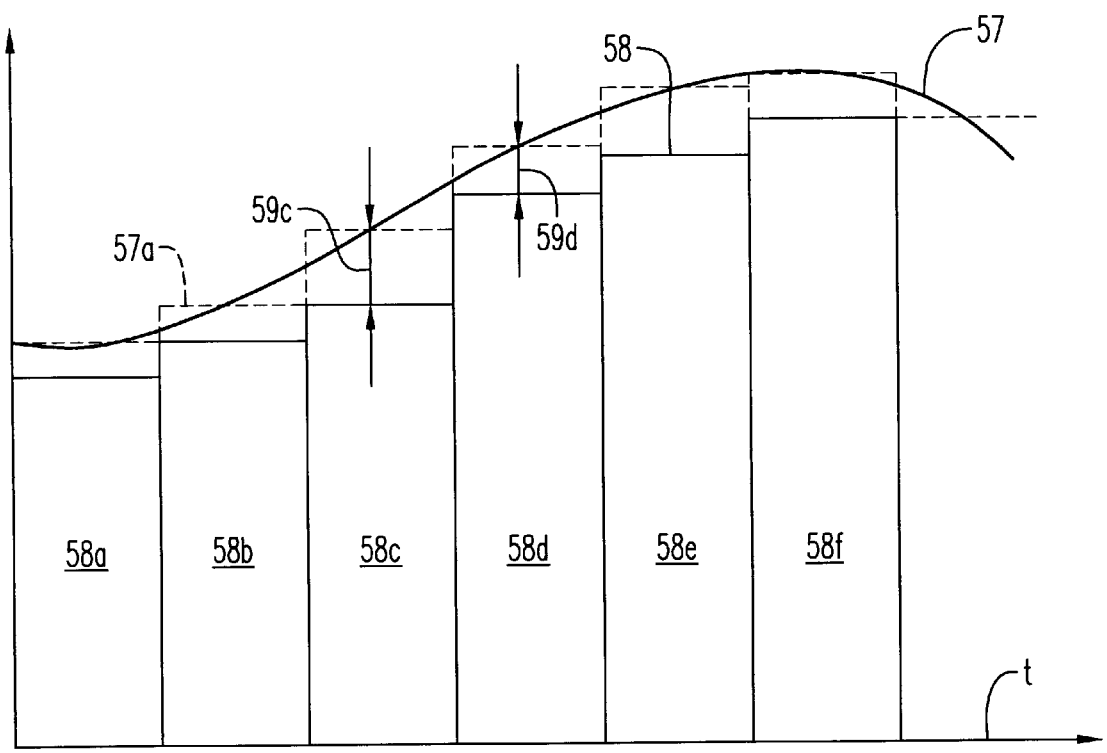
Figure 8:
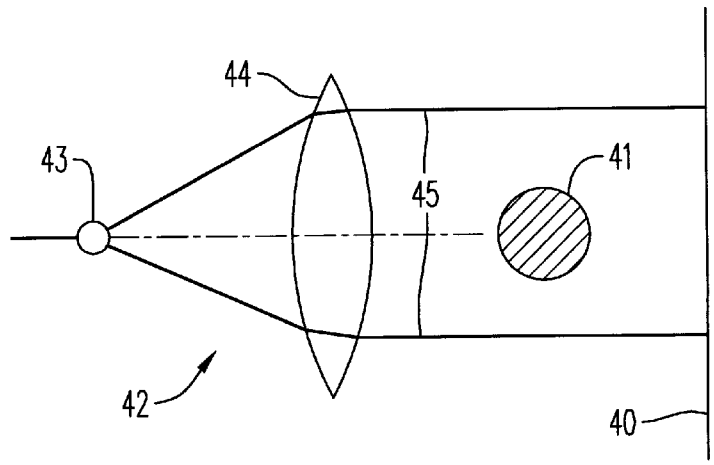
Figure 9:
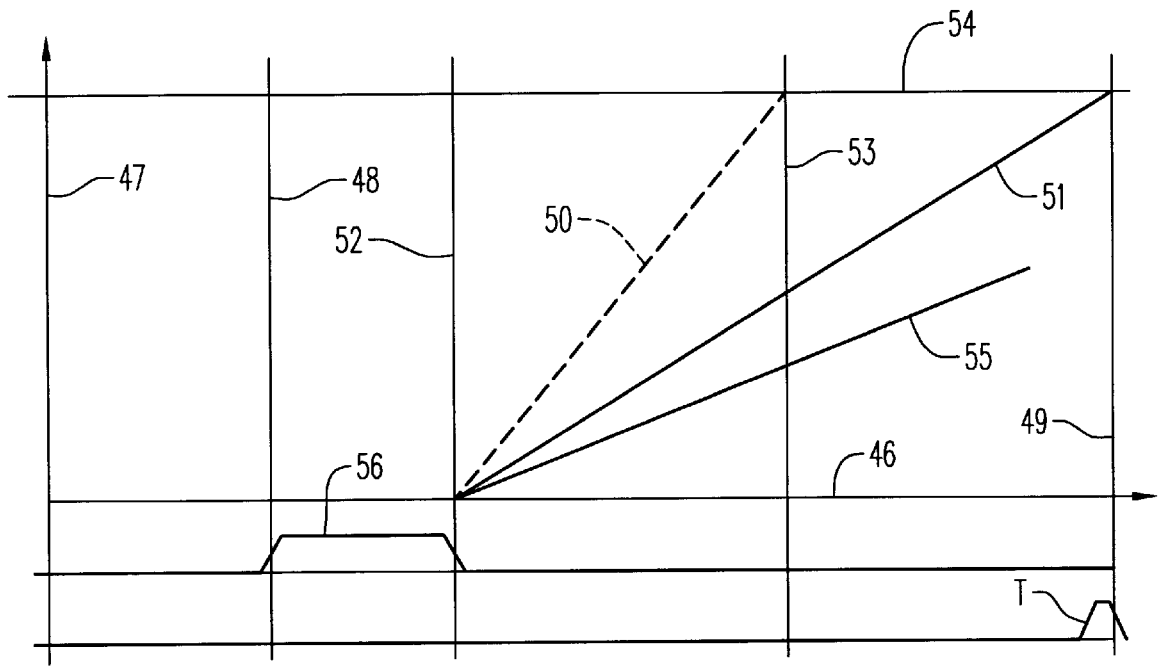
Figure 11:
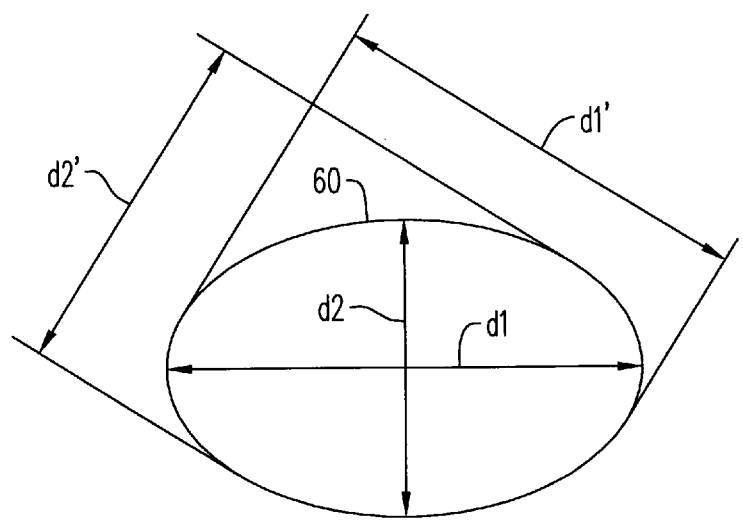

The invention will be described in greater detail below by mean of an example and with reference to the attached drawings, where FIGS. 1 to 4 each show a part of the device according to the invention in a simplified representation, FIGS. 5 to 8 each show a further part of the device, FIG. 9 is a diagrammatic view of a function of a part of the device, FIG. 10 shows an analog and a digital signal, FIG. 11 shows a cross-section through a thread-type material with possible dimensions, and FIGS. 12 and 13 each show a signal from the device.

FIG. 1 shows a sensor 1 which consists of a plurality of individual sensors 2a, 2b, 2c, 2d etc., which although they are offset relative to one another, are nevertheless disposed overlapping in certain areas when viewed in x direction and in y direction.

FIG. 2 shows a sensor 3 with individual sensors 3a, 3b, 3c, 3d as well as 3e and 3f, which are arranged in a row. In this case the individual sensors 3a–3d, for example, can operate digitally, while the individual sensors 3e and 3f can on the other hand operate by analog means. Thus a sensor 3 is obtained with individual sensors 3a, 3e which operate according to different principles, at least as regards the processing of the signals which they emit. The individual sensors are arranged in the direction of the parameter to be measured, here, as in FIG. 1, therefore, in the direction of the diameter or cross-section of the material K.

FIG. 3 shows a sensor 4 with individual sensors 5 and 6a 6k. Here, for example, the individual sensor 5 can operate by analog means and the individual sensors 6a–k operate together digitally, by the individual signals being combined into a digital signal.

FIG. 4 shows a further sensor 7 with individual sensors 8a, 8b and 9a–9e. As also with the sensor 4 (FIG. 3), the individual sensors 8 and 9 cover preferably the same metering section height, or are at least partly assigned to the same area of the material (here in y direction).

FIG. 5 shows sensors 10 and 11, which are arranged in two planes 12 and 13 inclined relative to one another.

FIG. 6 shows a measuring gap 14 such as is used conventionally for the measurement or inspection of yarn 15. The measuring gap 14 is bounded on each side by a cover glass 16, 17. On the other side of the cover glasses 16, 17 there extend focusing hoods or light guides 18, 19, which each lead to a transmitter 20, 21 and a detector 22, 23 for light signals. The light guides 18, 19 each comprise a mirror 24, 25, so that two ray paths 26, 27 are obtained which lead respectively from the transmitter 20, 21 via the mirrors 24, 25 and the yarn 15 to the detector 23, 22. The transmitters 20, 21 are preferably constructed in such a way that they send out light in a main direction. The detectors 22, 23 comprise preferably a telecentric optical detection system. Substantially parallel light beams therefore occur in the vicinity of the cover glasses 16, 17 and the measuring gap 14. The position of the yarn 15 in the measuring gap 14 can thus change without the size of the imaging of the yarn 15 onto the detectors 22, 23 changing. The scale therefore remains the same. It is also ensured by this arrangement that the orthogonal light beams in the measuring gap 14 scarcely influence one another and hence can be used simultaneously for the obtaining of measured values.

Figure 7:
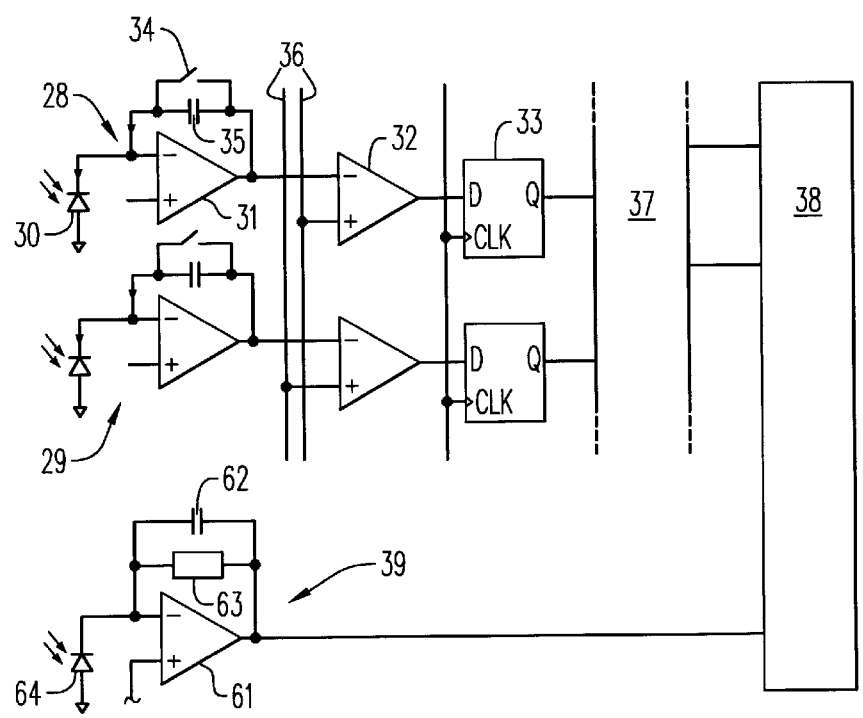

FIG. 7 shows two identically constructed circuits 28 and 29 such as can be provided for each individual sensor. One such consists of an element 30 for converting light into an electric current, for example a photodiode. Said element 30 is regarded preferably as an individual sensor in itself. The latter is connected in series with further elements for the conversion of its output signal, such as a charge amplifier 31, 35, a comparator 32 and a storage device or latch 33. The charge amplifier 31, which consists of an operational amplifier 31 and a capacitor 34 (in the feedback path), is further connected in parallel with a switch 34. The comparator 32 is connected with its input to a reference circuit 36. The storage device 33 is connected with its output to a multiplexer 37.

There is connected in series with the multiplexer 37 in turn an evaluation circuit 38, which can preferably be constructed as a computing element. Likewise connected to the evaluation circuit 38 is optionally a circuit 39 for generating an analog individual signal. The latter comprises in addition to an individual sensor 64 in particular an operational amplifier 61 with a parallel connected capacitor 62 and a resistor 63. Preferably at least one part of the aforementioned elements is integrated with the individual sensor 30, 64 to form an integrated circuit and thus forms a so-called "smart sensor".

FIG. 8 shows diagrammatically a surface 40 of one of the sensors, a thread-type material 41 in cross-section and a light source 42 for directed light. Said light source 42 can consist for example of a point-or line-shaped light source 43 and a telecentric optical detection system 44. Directed and preferably parallel beams 45 can be generated with it. FIG. 9 shows various lines which concern operations in the device and which are shown above a time axis 46 and next to an axis 47 which are entered along the values for electric voltages or percentages of possible values thereof. Line 48 marks for example the start and line 49 the end of a periodic cycle. Lines 50, 51 and 55 indicate the charging of the capacitor 35 over time in various situations, which start with a time corresponding to a line 52.

FIG. 10 shows in simplified form, plotted above a time axis t, an analog individual signal 57 and a digitized and clocked individual signal 58, which consists of individual values 58a to 58f. Due to the different principles which are used in the measurement or evaluation, differential values 59c, 59d etc. are for example obtained between the analog and the digital signal.

FIG. 11 shows a contour 70 of a cross-section of a thread-type material, which contour 70 is here assumed to be noncircular and in particular elliptical in shape. di and d2 are main dimensions, such as are determined along the main axes of the contour 60. di' and d2l are main dimensions such as are determined in two other, orthogonal directions.

FIG. 12 shows a representation of a thread-type material 65 which corresponds for example to the material K from FIG. 1, namely a representation such as is obtained by individual sensors 6 FIG. 3 with corresponding resolution for example in the evaluation circuit 38, in which several successive measurement cycles are stored. Here the individual sensors, such as e.g. the individual sensor 66, have smaller dimensions than the individual sensors 6 and 9 and there corresponds to each individual sensor or pixel in a storage device of the evaluation circuit 38 a storage space which is occupied with a binary signal. In order to obtain such a representation, several columns 67a, 67b, 67c, etc. are stored, wherein each column 67 pertains to a particular measurement cycle. Next to the actual material 65 and projecting from it, individual fibrils or fibers can be distinguished, which are labeled 68 and 69. The symbol 70 stands for a so-called erosion matrix, which is used for the carrying out of so-called neighborhood operations known per se. The latter consists here of thirteen pixels or storage spaces, which are arranged around a central pixel 71 on which the neighborhood operations is (sic) performed.

FIG. 13 shows a representation according to FIG. 12 in which the projecting fibrils or fibers are path-eroded by the neighborhood operations. Thus there is distinguished now only a large-area structure such as the actual material 72 whose diameter is reduced artificially by the erosion to some two pixels on each side.

The method of operation of the device is as follows:

As shown in FIG. 8, a thread-type material 41 such as e.g. a yarn, a fiber, a wire etc., such as is the case for example with known yarn testing units and yarn cleaners, is moved in a measuring gap in its longitudinal direction past a sensor whose surface 40 is represented here. The surface 40 is covered or shaded relative to the light source 42 by the material 41. Behind the surface 40 a sensor 13, 4 or 7 is provided, such as is known from one of FIGS. 1 to 4.

With the sensor 1 there can be recorded for example the diameter of a material K in y direction or the arrival of a material K in x direction. The material K covers, viewed from the light source in FIG. 1, two individual sensors completely and two only partially. Four individual sensors thus each emit an individual signal, which is influenced by the material K. Three individual sensors 2a, 2b, 2c emit an individual signal which is not influenced by the material K. An evaluation of the totaled eight individual signals enables a signal to be generated which is proportional to the diameter of the material K. The accuracy of the measurement depends on the number of individual sensors which are provided per unit of length or on whether the individual signals are intrinsically modulatable, i.e., are processed by analog means, or whether they are recorded only in binary form, so that a digital signal is obtained. A further possibility consists in configuring the sensor 1 in such a way that it records as a parameter only the position of the material K in y direction. Then for example the individual sensor 2c does not emit a signal which indicates shading by the material, whereas the individual sensor 2d emits such a signal. An external demarcation of the material K therefore lies between them.

With the sensor 3 (FIG. 2) the diameter of a material can be recorded as a parameter in the same manner as with the sensor 1. If it is assumed that the individual sensors 3a 3d emit individual signals which are recorded in binary form and that the individual sensors 3e and 3f emit individual signals which are recorded and further processed in analog form, a differentiated recording of edge areas of the material can thus be made possible. Or the diameter can be recorded with the individual sensors 3a–3d and the existence of projecting parts and their approximate dimensions be recorded with the individual sensors 3e and 3f. With the sensor 4 (FIG. 3) the diameter of the material can be recorded on the one hand digitally by the individual sensors 6a–6k and on the other in analog form by the individual sensor 5. The individual sensor 5 supplies an individual signal which is proportional to the shading by the material. The individual sensors 6 each supply an individual signal which, although it is likewise proportional to the shading, is however binarized, so that a digital signal is generated from the individual signals of the individual sensors 6. Comparison of the individual signal from the individual sensor 5 with the signal from the individual sensors 6 enables further parameters to be determined, such as the hairiness, structure etc. of the material, in particular if the material is a yarn.

With the sensor 7 (FIG. 4) the same measurements can in principle be carried out as with the sensor 4, except that the individual sensors 8 each emit an individual signal which is dependent on the position of the material in front of the individual sensors 8 in y direction. For example, if the material is at the bottom edge of the sensor 7, it then shades mainly the individual sensor 8b, so that the individual signal of the individual sensor 8b is influenced far more strongly than the individual signal of the individual sensor 8a. If the material is at the top edge of the sensor 7, the individual sensor 8a is influenced more strongly.

With a device according to FIG. 5, in which sensors 10 and 11 are arranged in two planes 12, 13, the material can be viewed from two directions, which permits more accurate conclusions as to the true cross-section of the material. There are provided as sensors 10, 11 sensors 1, 3, 4, 7 or others.

With the device according to FIG. 6 a material, here a yarn 15, can likewise be viewed from two directions, corresponding to the ray paths 26, 27. The transmitter 20 transmits a ray of light onto the mirror 24, which is passed from there onto the detector 23. At the same time the yarn 15 shades the detector 23, which consists of one of the sensors 1, 3, 4, 7. The transmitter 21 transmits a ray of light onto the mirror 25, which is passed from there onto the detector 22. At the same time the yarn 15 shades the detector 22, which consists of one of the sensors 1, 3, 4, 7. There is understood as a ray of light here a whole bundle of preferably directed and parallel rays, so that the yarn 15 is also detected if it is not located precisely at the point shown in the measuring gap 14.

If now an individual sensor is covered partly or completely by a material relative to a light source, a cycle takes place roughly as follows. At a time 48 (FIG. 9) said cycle starts by a reset signal 56 being triggered which closes the switch 34 (FIG. 7), keeps the latter closed and lasts up to a time 52, with which a start is therefore made on charging the capacitor or capacitors 35 by photocurrents from the individual sensor or sensors, or in other words on integrating the signal recorded.

If an individual sensor is not covered by the material 41 relative to the light source 42, the charging of the capacitor 35 proceeds rapidly, as is shown by the line 50, and is completed at the time 53 if a threshold S4 is reached. The operational amplifier 31 at the same time amplifies the signal from the capacitor 35 and passes it to the comparator 32. The latter compares continuously the signal according to line SO with a threshold value which is represented by a line 54 and sits close via a circuit 36. If the threshold value 54 is reached, the comparator 32 passes a signal to the storage device 33, which signal indicates that the individual sensor is not covered. Said signal has only two possible values and is a binary signal.

If an individual sensor is shaded by the material, it does not receive any direct light, but at best scattered light. The capacitor 3S is therefore only charged more slowly, for example according to a line 55, and reaches the threshold value 54 at best after a very long time which exceeds the cycle time. The signal recorded is therefore integrated during a predetermined time and then reset. The storage device 33, which operates with the same cycle time and is therefore clocked in synchrony with the switch 34, now receives from the comparator 32 a signal which indicates that the individual sensor is shaded and said signal can be outputted together with the signals from the storage devices of the other individual sensors. The multiplexer 37 produces from all the signals, by mounting the individual binary values side by side, an image of the illumination of the whole sensor. A value for the yarn cross-section can for example be obtained from this.

The cycle time is delimited by the lines 48 and 49. Depending on the quality of the individual sensor or the degree of fouling of the individual sensor, a greater or lesser time elapses until the charging of the capacitor 35 reaches the threshold value 54. The lines 49 and 51 indicate how long the charging of the capacitor 35 takes if only 50% of the possible light reaches the individual sensor. It can be adopted as an approach for the selection of the permitted time for the charging of the capacitor 35 that the reaching of the threshold value 54 at half output should still be possible within the cycle and hence the time 49. Due to displacement of the lines 52, 53 within the cycle time, this can be set by lengthening or shortening the duration of the reset signal 56, which also means that the reset signal 56 takes up the remaining part of the time in the cycle. Individual sensors which are not charged sufficiently in the time between the lines 49 and 52 are therefore regarded as covered by the material. If the fouling is insignificant and if a particularly good individual sensor is involved, the lines 52, 53 can be displaced in the direction of the line 49 and the lines 50, 51 can have a steeper course. These operations can be repeated for each individual sensor, there being determined as controlled variable that time which is required for the signal of the first of the individual sensors involved to reach the threshold 54. This time is regarded as the actual value for the control. Doubling the value of this time produces the illumination or integration time which lies between the lines 49 and 52. If the latter is too short, the first individual sensor reaches the threshold 54 too late, i.e. not until after more than half the time. The latter then simply has to be prolonged.

If it is assumed, for example, that with the sensor 4 there is generated by means of the individual sensor 5 and a circuit 39 (FIG. 7) an analog individual signal 57 (FIG. 10) which is proportional to the diameter of the material, and that there is generated by means of the individual sensors 6a–6k-and circuits 29, 30 etc. a digital individual signal which is likewise proportional to the diameter of the material, it is found that the two individual signals do not coincide exactly, even if they originate from the same material. Differential values 59 result for example from the fact that the individual sensors 5 and 6 do not record edge areas of the material equally. For example, the individual sensors 6 record in the case of a yarn rather the yarn package, whereas the individual sensor 5 records the yarn with projecting fibers. The differential values 59 can for example in the case of a yarn correspond to the hairiness and are determined as such in the computing element 38 from the individual signals 57 and 58 by subtraction. Two signals are therefore recorded in parallel from the same material. One of them is clocked.

With the device according to FIG. 5 the material can be recorded from two directions. If the cross-section of the material is to be determined as the parameter, two different diameters must be measured for this. There are various possible ways of doing this, as FIG. 11 shows. Main dimensions di and d2 or di' and d21 can be determined as diameters. As for example two directions are predetermined with the device according to FIG. 5, which for example are at right angles to one another, the uncertainty as to which dimensions will be recorded remains, since this depends on the chance position of the material. In order to reduce this effect as much as possible, the two dimensions recorded are to be computed twice, i.e. the product d1*d2 or d1f*d21 of the main dimensions and half the sum of the squares of the main dimensions, that is to say 0.5(d12+d22) or 0.5(d1'2+d2'2), is to be formed. This can be carried out in the evaluation circuit 38, to which all the individual sensors of the sensors 10 and 11 are connected. There can also be obtained from the two main dimensions data on parameters such as the roundness (circularity), or in the case of doubled yarns the doubling direction, by for example calculating the quotient of the small diameter and the large diameter, e.g. d2/d1.

Preferably the integrating individual sensors 5, 8, which emit an analog individual signal, are clocked with the same clock signal as the individual sensors 6, 9, which emit a digital signal. This then produces in FIG. 10 likewise a stepped curve 57a, which replaces the individual signal 57. Despite this, however, the stepped curve 57a is based on signals recorded and processed in analog form.

The individual signals from the individual sensors can optionally be further processed by neighborhood operations known per se. For this first of all the results of the digitizing individual sensors 6, 9 from some successive cycles are stored. The signals of each individual sensor from one of these cycles are recorded together with the neighboring signals, i.e. the signals of the same individual sensor in neighboring cycles and the signals of neighboring individual sensors in the same and in neighboring cycles, and compared with the relevant signal of the individual sensor. There is therefore also formed for each individual signal the environment, and individual signals of an individual sensor impinging from the environment are adjusted to the surrounding signals. Loose structures consisting of loosely cohering pixels are eliminated in this way, and only large-area structures, such as e.g. a yarn package, remain, as shown in FIG. 13.

What is claimed is:

1. A device for the optical recording of at least one parameter on a longitudinally moved thread-type material, including an optical sensor composed of at least two individual sensors, in which at least one individual sensor is so constructed and arranged that at least one measured value is digitally recorded for the parameter and one individual sensor is provided for the analog recording of a measured value for the parameter.

2. Device according to claim 1, characterized in that a plurality of individual sensors (2a–2c, 3a–3d, 6a 6k, 9a–9e) are provided for the direct digital recording of a measured value for the parameter.

3. Device according to claim 1, characterized in that the individual sensor (5, 8) for the analog recording and at least one individual sensor (6, 9) for the digital recording of a measured value for a parameter are assigned at least partly to the same area of the material.

4. Device according to claim 1, characterized in that there are assigned to the individual sensor for the digital recording, elements (31, 32) for converting its output signal into at least one binary signal, wherein at least one threshold value (54) is provided.

5. Device according to claim 4, characterized in that the elements (31, 32) are integrated on an integrated circuit with the individual sensor (30).

6. Device according to claim 1, characterized in that there is assigned to the sensors a light source (42) for directed light.

7. Device according to claim 1, characterized in that an optical sensor (10, 11) is disposed parallel to a first and to a second plane (12, 13) respectively.

8. A method for the optical recording of at least one parameter on a longitudinally moved thread-type material, including the step of recording at least two signals in parallel from the material at the same location and at the same time, wherein at least one of said signals is processed digitally and another of said signals is processed in an analog manner to form a measured value.

9. Method according to claim 8, characterized in that the signal recorded in clocked form is integrated during a preset time and reset after the predetermined time (48).

10. Method according to claim 9, characterized in that the signal recorded in clocked form is compared continuously with a threshold value (54) and an output signal is generated if the threshold value is reached within the pre-determined time.

11. Method according to claim 9, characterized in that the predetermined time is influenced by operations which include a light source (42) for illuminating the material and is changeable thereafter.

12. The method according to claim 8, in which the signal that is digitally processed is clocked.

* * * * *